United States Patent
Meister et al.

(10) Patent No.: US 11,235,149 B2
(45) Date of Patent: Feb. 1, 2022

(54) MULTICHANNEL OPTOGENETIC STIMULATION AND INHIBITION

(71) Applicant: MED-EL Elektromedizinische Geraete GmbH, Innsbruck (AT)

(72) Inventors: Dirk Meister, Innsbruck (AT); Darshan Shah, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 16/085,619

(22) PCT Filed: Apr. 13, 2017

(86) PCT No.: PCT/US2017/027312
§ 371 (c)(1),
(2) Date: Sep. 17, 2018

(87) PCT Pub. No.: WO2017/180809
PCT Pub. Date: Oct. 19, 2017

(65) Prior Publication Data
US 2019/0099600 A1    Apr. 4, 2019

Related U.S. Application Data

(60) Provisional application No. 62/322,266, filed on Apr. 14, 2016.

(51) Int. Cl.
*A61N 1/36*    (2006.01)
*A61N 1/372*    (2006.01)
(Continued)

(52) U.S. Cl.
CPC ......... *A61N 1/36038* (2017.08); *A61N 1/372* (2013.01); *A61N 5/0603* (2013.01);
(Continued)

(58) Field of Classification Search
CPC .. A61N 1/36038; A61N 1/372; A61N 5/0601; A61N 5/0613; A61N 5/062; A61N 5/0622
(Continued)

(56) References Cited

U.S. PATENT DOCUMENTS 8,948,877 B2    2/2015 Schleich et al.
2002/0198575 A1*    12/2002 Sullivan ............... A61N 5/0616
607/88
(Continued)

FOREIGN PATENT DOCUMENTS

EP    2 571 567 A1    3/2013

OTHER PUBLICATIONS

International Searching Authority/US, International Search Report and the Written Opinion of the International Searching Authority, Application No. PCT/US2017/027312, dated Jul. 7, 2017, 17 pages.
(Continued)

*Primary Examiner* — John R Downey
(74) *Attorney, Agent, or Firm* — Sunstein LLP

(57) ABSTRACT

Optogenetic signal processing is described for an auditory prosthesis with an intracochlear array of optical stimulation sources implanted in a patient having auditory neurons genetically modified with light sensitive ion channels. Stimulation timing signals are generated for the corresponding auditory neurons for each band pass signal based on characteristic temporal fine structure features of the band pass signals. The stimulation timing signals include: i. one or more channel opening signals adapted to open the ion channels of the corresponding auditory neurons, and ii. one or more channel closing signals adapted to close the ion channels of the corresponding ion channels. Optical stimulation signals are then produced for the optical stimulation sources based on the stimulation timing signals.

13 Claims, 5 Drawing Sheets

(51) Int. Cl.
*A61N 5/06* (2006.01)
*H04R 25/00* (2006.01)

(52) U.S. Cl.
CPC ........... *A61N 5/0622* (2013.01); *H04R 25/70* (2013.01); *A61N 2005/0605* (2013.01); *A61N 2005/0626* (2013.01); *A61N 2005/0629* (2013.01); *A61N 2005/0663* (2013.01); *H04R 2225/67* (2013.01)

(58) Field of Classification Search
USPC .......................................................... 607/88
See application file for complete search history.

(56) References Cited

U.S. PATENT DOCUMENTS

| | | | | |
|---|---|---|---|---|
| 2004/0093043 | A1* | 5/2004 | Edel | A61N 5/062 |
| | | | | 607/88 |
| 2008/0319509 | A1* | 12/2008 | Laback | A61N 1/36036 |
| | | | | 607/57 |
| 2009/0036962 | A1* | 2/2009 | Zierhofer | A61N 1/0541 |
| | | | | 607/137 |
| 2011/0004274 | A1 | 1/2011 | Schleich et al. | |
| 2011/0125077 | A1* | 5/2011 | Denison | A61N 5/0622 |
| | | | | 604/20 |
| 2012/0253261 | A1* | 10/2012 | Poletto | A61N 5/0601 |
| | | | | 604/20 |
| 2013/0218236 | A1 | 8/2013 | Churchill | |
| 2013/0296976 | A1* | 11/2013 | Maxik | H05B 45/20 |
| | | | | 607/88 |
| 2014/0128941 | A1* | 5/2014 | Williams | H05B 45/46 |
| | | | | 607/88 |
| 2015/0005845 | A1 | 1/2015 | Frühauf et al. | |
| 2015/0100011 | A1 | 4/2015 | Kumar et al. | |
| 2016/0016006 | A1 | 1/2016 | Boyle | |
| 2017/0001007 | A1* | 1/2017 | Meister | A61N 1/36038 |
| 2017/0080228 | A1* | 3/2017 | Meister | A61N 1/36036 |

OTHER PUBLICATIONS

European Patent Office, Extended European Search Report, Application No. 17783094.0, dated Aug. 26, 2019, 11 pages.

Ingeborg Hochmair et al., *MED-EL Cochlear Implants: State of the Art and a Glimpse Into the Future*, Trends in Amplification, vol. 10, No. 4, Dec. 1, 2006, pp. 201-219.

* cited by examiner

MULTICHANNEL OPTOGENETIC STIMULATION AND INHIBITION

This application claims priority from U.S. Provisional Patent Application 62/322,266, filed Apr. 14, 2016, which is incorporated herein by reference in its entirety.

TECHNICAL FIELD

The present invention relates to hearing implant systems, and more specifically, to techniques for producing electrical stimulation signals in such systems.

BACKGROUND ART

A normal ear transmits sounds as shown in FIG. 1 through the outer ear 101 to the tympanic membrane (eardrum) 102, which vibrates the ossicles of the middle ear 103 (malleus, incus, and stapes). The stapes footplate is positioned in the oval window 106 that forms an interface to the fluid filled inner ear (the cochlea) 104. Movement of the stapes generates a pressure wave in the cochlea 104 that stimulates the sensory cells of the auditory system (hair cells). The cochlea 104 is a long narrow duct wound spirally around its central axis (called the modiolus) for approximately two and a half turns. The cochlea 104 includes an upper channel known as the scala vestibuli, a middle channel known as the scala media and a lower channel known as the scala tympani. The hair cells connect to the spiral ganglion cells of the cochlear nerve 105 that reside in the modiolus. In response to received sounds transmitted by the middle ear 103, the fluid-filled cochlea 104 functions as a transducer to generate electric pulses which are transmitted to the cochlear nerve 105, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

A typical cochlear implant system includes an external microphone that provides an audio signal input to an external signal processor where various signal processing schemes can be implemented. The processed signal is then converted into a digital data format, such as a sequence of data frames, for transmission into the implant. Besides receiving the processed audio information, the implant also performs additional signal processing such as error correction, pulse formation, etc., and produces a stimulation pattern (based on the extracted audio information) that is sent through an electrode lead to an implanted electrode array.

Typically, the electrode array includes multiple electrode contacts on its surface that provide selective stimulation of the cochlea. Depending on context, the electrode contacts are also referred to as electrode channels. In cochlear implants today, a relatively small number of electrode channels are each associated with relatively broad frequency bands, with each electrode contact addressing a group of neurons with an electric stimulation pulse having a charge that is derived from the instantaneous amplitude of the signal envelope within that frequency band.

FIG. 2 shows various functional blocks in a signal processing arrangement for producing electrode stimulation signals to electrode contacts in an implanted cochlear implant array according to a typical hearing implant system. A pseudo code example of such an arrangement can be set forth as:

Input Signal Preprocessing:
    BandPassFilter (input_sound, band_pass_signals)
Envelope Extraction:
    BandPassEnvelope (band_pass_signals, band_pass_envelopes)
Stimulation Timing Generation:
    TimingGenerate (band_pass_signals, stim_timing)
Pulse Generation:
    PulseGenerate (band_pass_envelopes, stim_timing, out_pulses)

The details of such an arrangement are set forth in the following discussion.

In the signal processing arrangement shown in FIG. 2, the initial input sound signal is produced by one or more sensing microphones, which may be omnidirectional and/or directional. Preprocessor Filter Bank 201 pre-processes this input sound signal with a bank of multiple parallel band pass filters (e.g. Infinite Impulse Response (IIR) or Finite Impulse Response (FIR)), each of which is associated with a specific band of audio frequencies, for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 201. The Preprocessor Filter Bank 201 also may perform other initial signal processing functions such as and without limitation automatic gain control (AGC) and/or noise reduction and/or wind noise reduction and/or beamforming and other well-known signal enhancement functions. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $U_1$ to $U_K$ (which can also be thought of as electrode channels) are output to a Stimulation Timer 206 that includes an Envelope Detector 202 and Fine Structure Detector 203. The Envelope Detector 202 extracts characteristic envelope signals outputs $Y_1, \ldots, Y_K$ that represent the channel-specific band pass envelopes. The envelope extraction can be represented by $Y_k = LP(|U_k|)$, where $|.|$ denotes the absolute value and $LP(.)$ is a low-pass filter; for example, using 12 rectifiers and 12 digital Butterworth low pass filters of 2nd order, IIR-type. Alternatively, the Envelope Detector 202 may extract the Hilbert envelope, if the band pass signals $U_1, \ldots, U_K$ are generated by orthogonal filters.

The Fine Structure Detector 203 functions to obtain estimates of the instantaneous frequencies in the signal channels, processing selected temporal fine structure features of the band pass signals $U_1, \ldots, U_K$ to generate stimulation timing signals $X_1, \ldots, X_K$. The band pass signals $U_1, \ldots, U_k$ can be assumed to be real valued signals, so in the specific case of an analytic orthogonal filter bank, the Fine Structure Detector 203 considers only the real valued part of $U_k$. The Fine Structure Detector 203 is formed of K independent, equally-structured parallel sub-modules.

The extracted band-pass signal envelopes $Y_1, \ldots, Y_K$ from the Envelope Detector 202, and the stimulation timing signals $X_1, \ldots, X_K$ from the Fine Structure Detector 203 are output from the Stimulation Timer 206 to a Pulse Generator 204 that produces the electrode stimulation signals Z for the electrode contacts in the implanted electrode array 205. The Pulse Generator 204 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 204 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties).

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate may be chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 μs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference. The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

Many cochlear implant coding strategies use what is referred to as an n-of-m approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

Conventional cochlear implants using electrical stimulation of the auditory nerve are limited in their spatial resolution due to the wide spread of electrical current, as illustrated in FIG. 3A. Various attempts have been made to reduce so called channel interactions/crosstalk due to electrical current spread. One simple method is to stimulate sequentially in time, as performed by traditional CIS stimulation, with electrode contacts that are locally separated. This maximizes the number of exited neurons because they are more likely to be out of their refractory state if the time of previous stimulation is maximized, but still the spread of excitation hampers the number of effective spectral channels. Sharpening of the electrical field is another attempt to provide more spectral channels. This is performed with so called focused stimulation like phased array or tripolar stimulation. Benefits of focused stimulation are limited as this consumes a lot of energy. For providing a loudness percept comparable to unfocused stimulation, the current level has to be raised so that the spread is also comparable to unfocused stimulation.

Another newer approach known as optogenetic stimulation is based on optical stimulation of genetically modified ion channels in auditory neurons (e.g. by viral expression of opsins such as Channelrhodopsin-2, Chronos, etc.) which is applied with an intracochlear array with multiple light sources as shown in FIG. 3B. Optogenetic stimulation is thought to provide more spatially focused stimulation of the auditory neurons than electrical stimulation and therefore should provide more distinct spectral channels. Different types of light sources can be in included in this intracochlear array that can produce different wavelengths of light, which can have different effects on the genetically modified ion channels.

For example, one wavelength of light might open ion channels and another wavelength might close them (Jeschke, Marcus, and Tobias Moser. "Considering optogenetic stimulation for cochlear implants." *Hearing research* 322 (2015): 224-234; incorporated herein by reference in its entirety). Ritter et al found that electrical conductivity of CHR2 may be switched on and off by alternating blue and green light (Ritter, Eglof, et al. "Light-dark adaptation of channelrhodopsin C128T mutant." *Journal of Biological Chemistry* 288.15 (2013): 10451-10458; Berndt, André, et al. "Bi-stable neural state switches." *Nature neuroscience* 12.2 (2009): 229-234; both of which are incorporated herein by reference in their entireties). Auditory neurons that express halorhodopsins (HaloR) can be silenced with yellow light (Zhao, Shengli, et al. "Improved expression of halorhodopsin for light-induced silencing of neuronal activity." *Brain cell biology* 36.1-4 (2008): 141-154; incorporated herein by reference in its entirety). Bimodal neural excitation also has been shown using red and blue light (S child, Lisa C., and Dominique A. Glauser. "Dual color neural activation and behavior control with chrimson and CoChR in Caenorhabditis elegans."*Genetics* 200.4 (2015): 1029-1034; incorporated herein by reference in its entirety). Currently efforts are also being made to look into an optogenetic toolbox for fast inhibition, excitation and bistable modulation (Prakash, Rohit, et al. "Two-photon optogenetic toolbox for fast inhibition, excitation and bistable modulation." *Nature methods* 9.12 (2012): 1171-1179; incorporated herein by reference in its entirety).

SUMMARY

Embodiments of the present invention are directed to optogenetic signal processing for an auditory prosthesis with an intracochlear array of a plurality of optical stimulation sources implanted in a patient having auditory neurons genetically modified with light sensitive ion channels. An input sound signal is processed to generate band pass signals, each representing a given band of audio frequencies and associated with a set of corresponding auditory neurons. Stimulation timing signals are then generated for the corresponding auditory neurons for each band pass signal based on characteristic temporal fine structure features of the band pass signals. The stimulation timing signals include: i. one or more channel opening signals adapted to open the ion channels of the corresponding auditory neurons to activate neural excitation, and ii. one or more channel closing signals adapted to close the ion channels of the corresponding ion channels to inhibit neural excitation. Optical stimulation signals are then produced for the optical stimulation sources based on the stimulation timing signals.

In some specific embodiments, the optical stimulation sources are configured to produce optical stimulation signals at a plurality of different wavelengths. For example, the channel opening signals may use optical stimulation signals having a first wavelength associated with opening the ion channels and the channel closing signals may use optical stimulation signals have a second wavelength different from the first wavelength and associated with closing the ion channels. The optical stimulation sources may be configured along the intracochlear array so as to alternate between the first wavelength and the second wavelength. For each ion channel, the channel opening signals and the channel closing signals may be adapted to be spatially distributed from each other.

The temporal fine structure features may include fine structure zero crossings, and for each ion channel, the channel opening signals and the channel closing signals may alternate based on the fine structure zero crossings. Each optical stimulation signal may have a fixed intensity, or a variable intensity that follows slope of a corresponding fine structure feature. Simultaneously or just prior to applying channel opening signals to a given ion channel, channel closing signals may be applied to one or more adjacent ion channels.

DETAILED DESCRIPTION

Embodiments of the present invention are directed to an optogenetic cochlear implant system with an intracochlear array of multiple optical stimulation sources that is implanted in a patient whose auditory neurons have been genetically modified with light sensitive ion channels. The auditory neuron ion channels can be opened and closed by different wavelength optical stimulation signals that are developed based on fine structure features of the band pass signals. Such systems offer high spatial selectivity and the possibility of using a greater number of spectral channels. In addition, higher stimulation rates can be implemented since the neural firing rate depends mainly on the time that the ion channels remain open.

Figure 1:
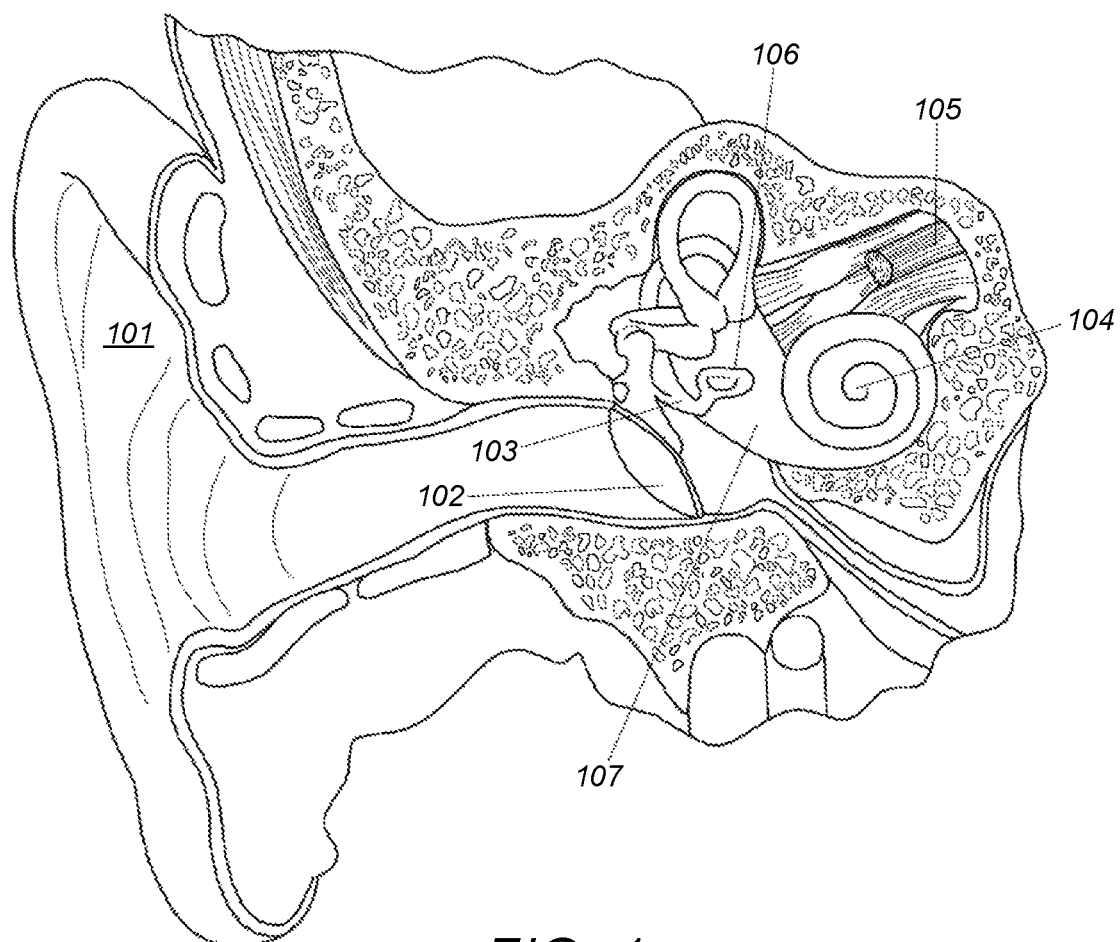
FIG. 1 shows anatomical structures of a typical human ear with a cochlear implant system.
Figure 2:
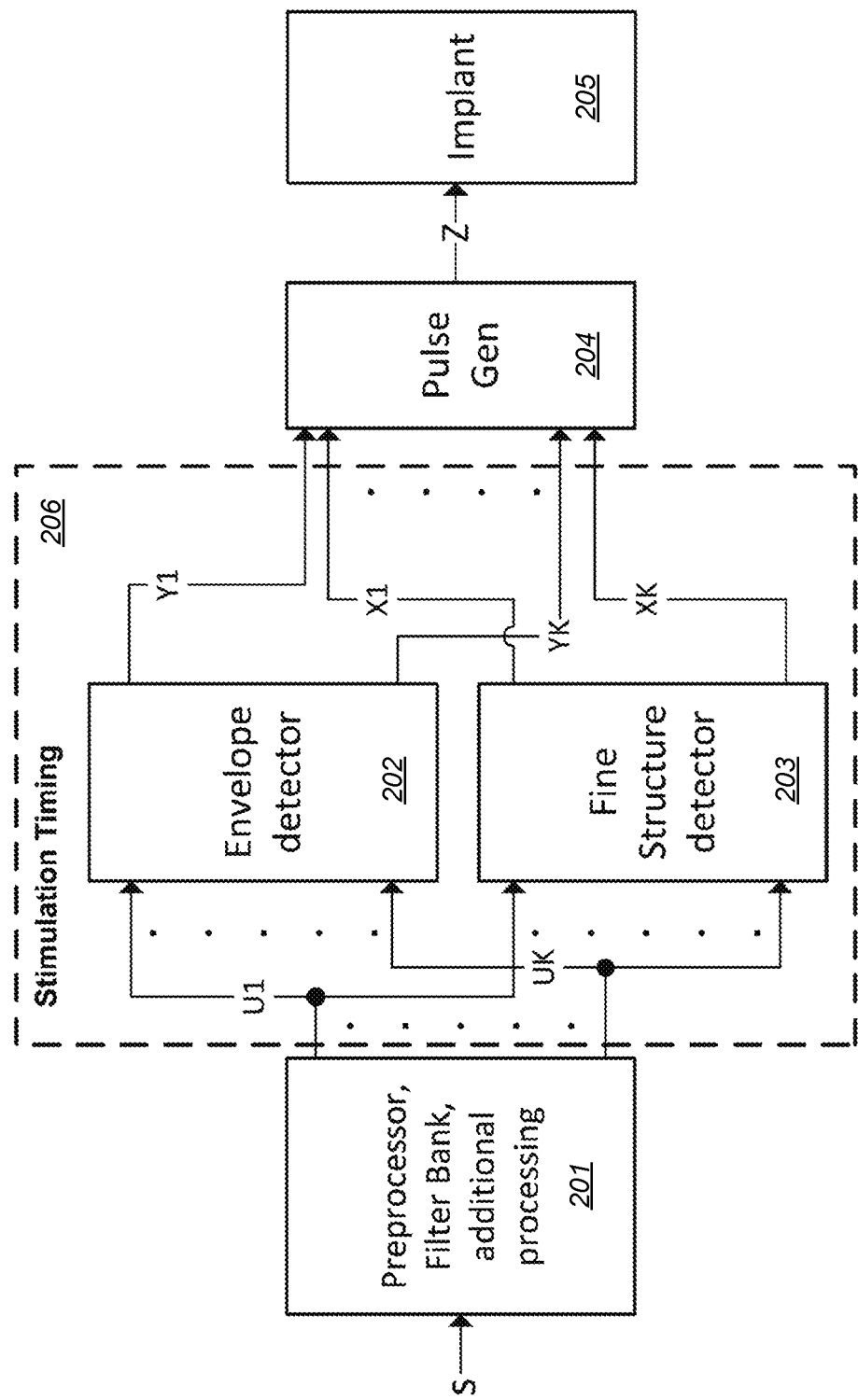
FIG. 2 shows various functional blocks in a signal processing arrangement for a typical cochlear implant system.
Figure 3A:
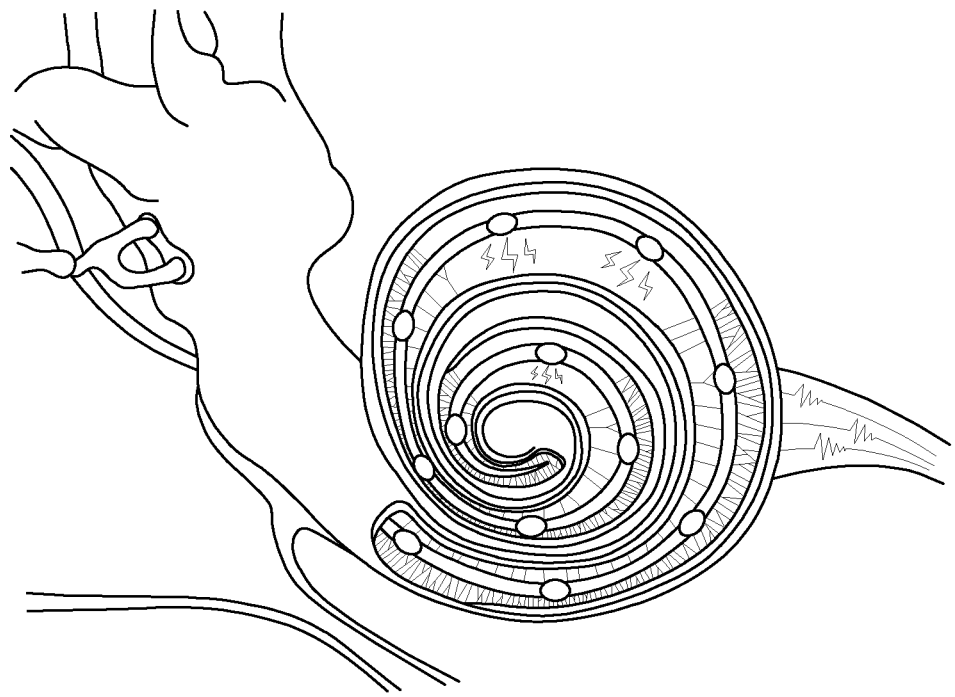
FIGS. 3A-3B show spatial spread characteristics of cochlear stimulation with electrical signals and optical signals.
Figure 3B:
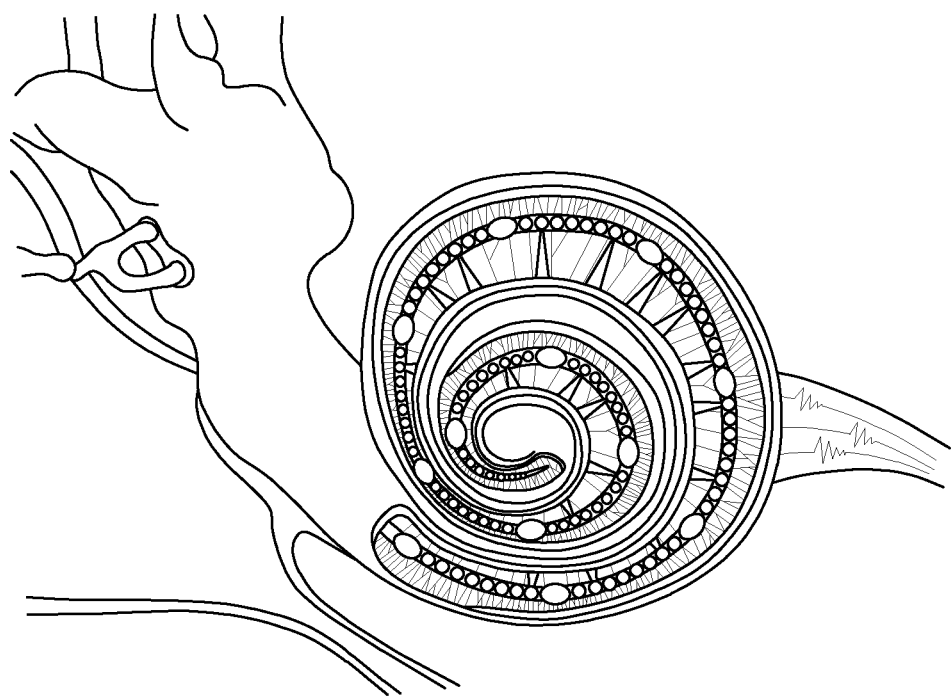

The functional signal processing blocks in such systems at a high level look like those in a conventional electrical stimulation-based cochlear implant such as discussed above with respect to FIG. 2. In such a system, a Preprocessor Filter Bank 201 processes an input sound signal to generate band pass signals, which each represent a given band of audio frequencies and which also are associated with a set of corresponding auditory neurons.

A Stimulation Timer 206 then generates optical stimulation timing signals for the corresponding auditory neurons for each band pass signal based on characteristic temporal fine structure features of the band pass signals similar to what is done in electrical stimulation arrangements such as FSP and FS4 schemes. But instead of generating electrical stimulation signals, the optical stimulation timing signals include one or more channel opening signals that are adapted to open the ion channels of the corresponding auditory neurons to activate neural excitation, and one or more channel closing signals that are adapted to close the ion channels of the corresponding ion channels to inhibit neural excitation.

Figure 4:
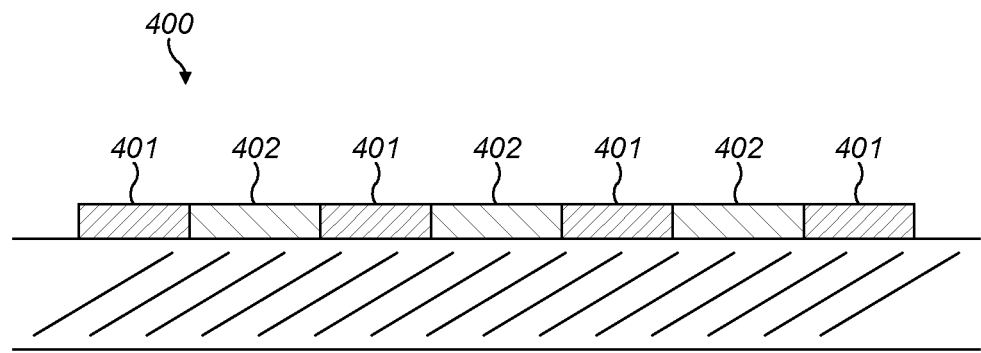
FIG. 4 shows an example of an intracochlear optical stimulation array suitable for embodiments of the present invention.

A Pulse Generator 204 then uses the stimulation timing signals to produce optical stimulation signals for the optical stimulation sources that are spatially distributed along an implanted intracochlear array. FIG. 4 shows an example of an intracochlear optical stimulation array 400 suitable for embodiments of the present invention which alternates channel opening signals from opening sources (OS) 401 and channel closing signals from closing sources (CS) 402, which can be realized, for example, by different wavelength blue and green microLEDs. The area of the neural population that the channel closing signals from the CS 402 can close spreads so that two flanking CS 402 will cover the same area that the in-between OS 401 can activate with the channel opening signals. In other words, neural ion channels that are opened by a channel opening signal for an OS 401, are closed with the two simultaneous channel closing signals of the flanking CS 402.

To enhance spatial selectivity, channel closing signals can be applied simultaneously or shortly before a channel opening signal on the light sources further away, e.g. the +1 neighboring light sources in order of inhibition. Alternatively, flanking light sources can be activated with reduced amplitude simultaneously or shortly before a channel opening signal so that the neural population that is intended to be stimulated by the channel opening signal is not covered by the channel closing signals. The channel opening and closing signals can specifically be either a continuous optical signal, or a sequence of optical pulses, and the signals can be scaled either with the amplitude of the signal envelope, or with the amplitude of the peak of the band pass signal.

Figure 5A:
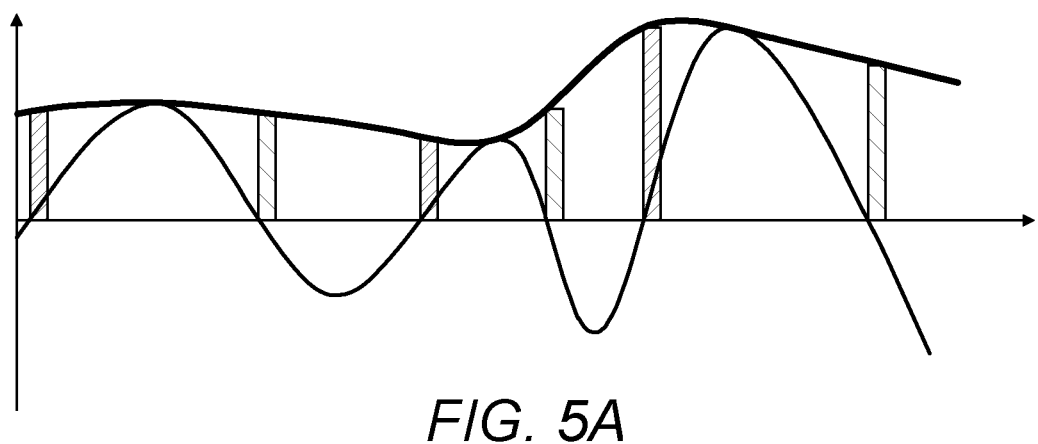
FIGS. 5A-5D show examples of optical stimulation patterns based on band pass fine structure according to embodiments of the present invention.
Figure 5B:
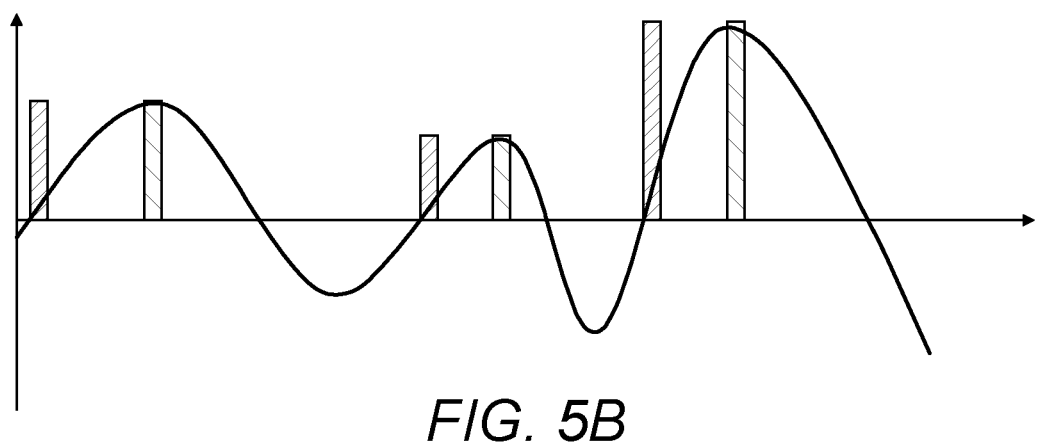

FIGS. 5A-5D show examples of optical stimulation patterns based on band pass fine structure according to embodiments of the present invention, in which the temporal fine structure features include fine structure zero crossings. For each ion channel, the channel opening signals and the channel closing signals alternate based on the fine structure zero crossings within each channel. As shown in FIG. 5A, for each negative to positive zero-crossing, a fixed intensity channel opening signal is applied, and for each positive to negative zero-crossing, a fixed intensity channel closing signal is applied. In another embodiment, the fixed intensity channel opening and/or closing signal may depend on the channel envelope or fine structure signal of the band pass signal. The intensity of the optical stimulation signal may be the strength of the optical stimulation pulse and/or the pulse duration.

Figure 5C:
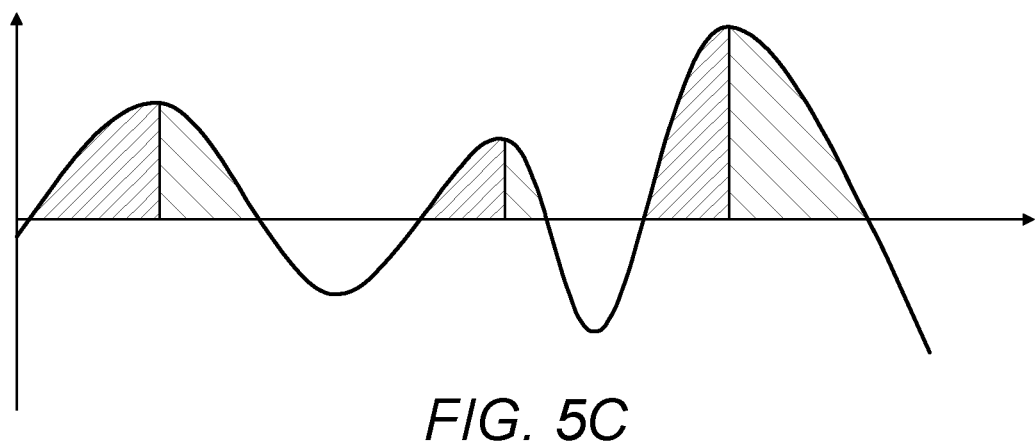
Figure 5D:
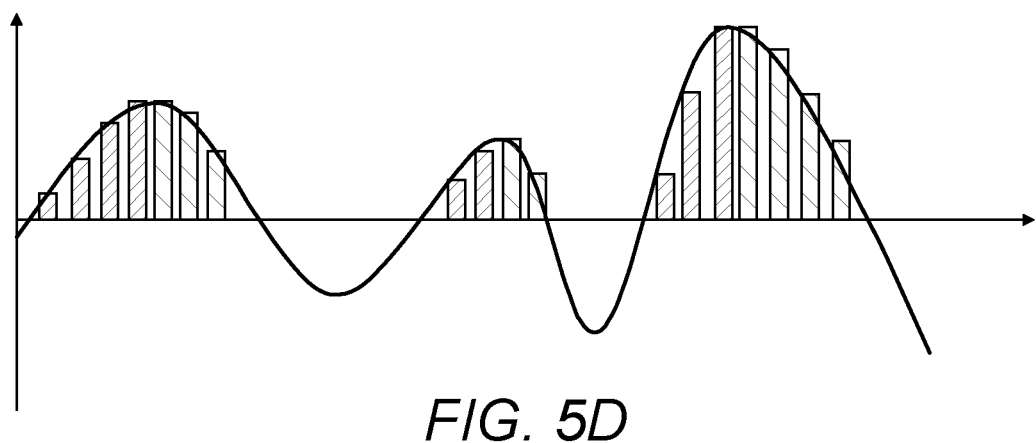

Another approach is shown in FIG. 5C where the intensity of the optical stimulation signals follows the slope of the band pass signal. Thus, at the negative to positive zero-crossing, the channel opening signal intensity is at a minimum, and then steadily rises with the band pass fine structure amplitude up to a maximum at the peak of the band pass signal. At that point the channel opening signal then is turned off and the channel closing signal is turned on that closes the ion channels and inhibits the neural excitation. FIG. 5D shows a similar approach using a series of short pulses as the channel opening signal starting at negative to positive zero-crossings until the peak of the band pass signal, then either a short pulse or a sequence of pulses is applied as the channel closing signal until the positive to negative zero crossing of the band pass signal.

Besides the zero-crossing approaches described above, CIS-type stimulation can be applied to some or all of the ion channels using a fixed time grid or stimulation frame that is amplitude modulated, for example, with the band pass envelope.

In another alternative, fast opening and closing of the ion channels can be promoted by applying an alternating order of channel opening signals on a given ion channel x, followed by channel closing signals on the flanking channels. So for an embodiment with nine optical stimulation sources which are arranged alternating and starting with an OS, then the light sources could be described as:

CS1, OS1, CS2, OS2, CS3, OS3, CS4, OS4, CS5

A corresponding stimulation frame would then look like:

[OS1], [CS1, CS2], [OS2], [CS2,CS3], [OS3], [CS3, CS4], [OS4], [CS4,CS5]

where the channels in brackets are stimulated simultaneously.

In another alternative, the ion channels may use different opsins or genes each associated with opening or closing the ion channels at different rates. For example two different opsins and/or genes opening the ion channels with different wavelength of the optical stimulation signal might be used to control the opening rate. It may be possible to use opsins or genes opening the ion channels with the same wavelength but different strength of the optical stimulation signal. For example up to a first optical stimulation strength only the opsin/gene with the low opening rate opens the ion channel and for any optical stimulation signal beyond that stimulation strength the opsin/gene with the high opening rate opens the ion channel. This may help to control modulating the intensity and perception of sound heard to a greater extent and thereby increases the dynamic range by controlling neural excitation.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of optogenetic signal processing for an auditory prosthesis with an intracochlear array of a plurality of optical stimulation sources implanted in a patient having auditory neurons genetically modified with light sensitive ion channels, the method comprising:

processing an input sound signal to generate a plurality of band pass signals, each band pass signal representing a given band of audio frequencies and associated with a set of corresponding auditory neurons, wherein each band pass signal has characteristic temporal fine structure features;

generating stimulation timing signals for the corresponding auditory neurons for each band pass signal based on the characteristic temporal fine structure features, wherein the stimulation timing signals include:
   i. one or more channel opening signals adapted to open the ion channels of the corresponding auditory neurons to activate neural excitation, and
   ii. one or more channel closing signals adapted to close the ion channels of the corresponding auditory neurons to inhibit neural excitation,
   wherein the channel opening signals use optical stimulation signals having a first wavelength associated with opening the ion channels and the channel closing signals use optical stimulation signals having a second wavelength different from the first wavelength and associated with closing the ion channels, and
   wherein the optical stimulation sources are configured along the intracochlear array so as to alternate between the first wavelength and the second wavelength; and producing optical stimulation signals for the optical stimulation sources based on the stimulation timing signals.

2. The method according to claim 1, wherein for each ion channel, the channel opening signals and the channel closing signals are adapted to be spatially distributed from each other.

3. The method according to claim 1, wherein the temporal fine structure features include fine structure zero crossings, and wherein for each ion channel, the channel opening signals and the channel closing signals alternate based on the fine structure zero crossings.

4. The method according to claim 1, wherein each optical stimulation signal has a fixed intensity.

5. The method according to claim 1, wherein each optical stimulation signal has a variable intensity following slope of a corresponding fine structure feature.

6. The method according to claim 1, wherein simultaneously or just prior to applying channel opening signals to a given ion channel, channel closing signals are applied to one or more adjacent ion channels.

7. An optogenetic signal processing system for an auditory prosthesis with an intracochlear array of a plurality of optical stimulation sources implanted in a patient having auditory neurons genetically modified with light sensitive ion channels, the system comprising:
   a preprocessor filter bank configured to generate a plurality of band pass signals, each band pass signal representing a given band of audio frequencies and associated with a set of corresponding auditory neurons, wherein each band pass signal has characteristic temporal fine structure features;
   a stimulation timer configured to generate stimulation timing signals for the corresponding auditory neurons for each band pass signal based on the characteristic temporal fine structure features, wherein the stimulation timing signals include:
      i. one or more channel opening signals adapted to open the ion channels of the corresponding auditory neurons to activate neural excitation, and
      ii. one or more channel closing signals adapted to close the ion channels of the corresponding auditory neurons to inhibit neural excitation,
      wherein the channel opening signals use optical stimulation signals having a first wavelength associated with opening the ion channels and the channel closing signals use optical stimulation signals having a second wavelength different from the first wavelength and associated with closing the ion channels, and
      wherein the optical stimulation sources are configured along the intracochlear array so as to alternate between the first wavelength and the second wavelength; and
   a pulse generator configured to generate optical stimulation signals for the optical stimulation sources based on the stimulation timing signals.

8. The system according to claim 7, wherein the plurality of optical stimulation sources are configured so that for each ion channel, the channel opening signals and the channel closing signals are spatially distributed from each other.

9. The system according to claim 7, wherein the temporal fine structure features include fine structure zero crossings, and wherein for each ion channel, the channel opening signals and the channel closing signals alternate based on the fine structure zero crossings.

10. The system according to claim 7, wherein each optical stimulation signal has a fixed intensity.

11. The system according to claim 7, wherein each optical stimulation signal has a variable intensity following slope of a corresponding fine structure feature.

12. The system according to claim 7, wherein simultaneously or just prior to applying channel opening signals to a given ion channel, channel closing signals are applied to one or more adjacent ion channels.

13. A non-transitory tangible computer-readable medium having instructions thereon for optogenetic signal processing for an auditory prosthesis with an intracochlear array of a plurality of optical stimulation sources implanted in a patient having auditory neurons genetically modified with light sensitive ion channels, the instructions comprising:
   processing an input sound signal to generate a plurality of band pass signals, each band pass signal representing a given band of audio frequencies and associated with a set of corresponding auditory neurons, wherein each band pass signal has characteristic temporal fine structure features;
   generating stimulation timing signals for the corresponding auditory neurons for each band pass signal based on the characteristic temporal fine structure features, wherein the stimulation timing signals include:
      i. one or more channel opening signals adapted to open the ion channels of the corresponding auditory neurons to activate neural excitation, and
      ii. one or more channel closing signals adapted to close the ion channels of the corresponding ion channels to inhibit neural excitation,
      wherein the channel opening signals use optical stimulation signals having a first wavelength associated with opening the ion channels and the channel closing signals use optical stimulation signals having a second wavelength different from the first wavelength and associated with closing the ion channels, and wherein the optical stimulation sources are configured along the intracochlear array so as to alternate between the first wavelength and the second wavelength; and producing optical stimulation signals for the optical stimulation sources based on the stimulation timing signals.

* * * * *

UNITED STATES PATENT AND TRADEMARK OFFICE
CERTIFICATE OF CORRECTION

PATENT NO. : 11,235,149 B2
APPLICATION NO. : 16/085619
DATED : February 1, 2022
INVENTOR(S) : Meister et al.

It is certified that error appears in the above-identified patent and that said Letters Patent is hereby corrected as shown below:

In the Claims

In Column 10, Line 59 Claim 13:
Replace "ion channels" with --auditory neurons--

Signed and Sealed this
Nineteenth Day of April, 2022

Katherine Kelly Vidal
*Director of the United States Patent and Trademark Office*